United States Patent [19]

Kabara

[11] 4,002,775
[45] Jan. 11, 1977

[54] FATTY ACIDS AND DERIVATIVES AS ANTIMICROBIAL AGENTS

[76] Inventor: Jon J. Kabara, 2088 Riverwood, Okemos, Mich. 48864

[22] Filed: May 21, 1975

[21] Appl. No.: 579,687

Related U.S. Application Data

[63] Continuation-in-part of Ser. No. 377,187, July 9, 1973, abandoned.

[52] U.S. Cl. .............................................. 426/532
[51] Int. Cl.$^2$ .................... A23L 3/34; A61K 31/23; A61K 31/22
[58] Field of Search ............ 424/312, 314; 426/532

[56] References Cited
UNITED STATES PATENTS 3,485,639  12/1969  Knightly ............................ 426/532

OTHER PUBLICATIONS

Goldsmith, Chemical Reviews, vol. 33, Aug.–Dec. 1943, pp. 257, 323, 329 & 331.
Atherton et al., Drug and Cosmetic Industry, vol. 100, Mar. 1967, pp. 50, 52, 54, & 162–166.
Akiko et al., Chem. Abst., vol. 75 (1971), p. 1777u.
Madli et al., Chem. Abst., vol. 72 (1970), p. 20,277k.
Pomeranz et al., Chem. Abst., vol. 72 (1970), p. 65523d.

*Primary Examiner*—Sam Rosen
*Attorney, Agent, or Firm*—Murray and Whisenhunt

[57] ABSTRACT

There is provided a food-grade microbicidal or microbiostatic composition containing a food or food-grade material and as the primary microbicide a monoester of a polyol and a twelve carbon atom aliphatic fatty acid.

4 Claims, 3 Drawing Figures

FATTY ACIDS AND DERIVATIVES AS ANTIMICROBIAL AGENTS

This is a continuation-in-part of copending application Ser. No. 377,187, filed on July 9, 1973, now abandoned, and entitled FATTY ACIDS AND DERIVATIVES AS ANTIMICROBIAL AGENTS.

The present invention is concerned with compositions and methods for producing microbicidal and/or microbiostatic effects on materials and animals, including humans. More particularly, the invention is concerned with such compositions and methods which use certain long chain fatty acid esters as the primary microbicide or microbiostatic ingredients.

BACKGROUND OF THE INVENTION

Various microbicidal and microbiostatic compositions are known for use in a variety of prophylactic applications. These compositions, however, suffer from disadvantages in that the compositions may be active toward only a narrow range of microbes or have low activity, requiring inordinate amounts for useful effects. Some of the known compositions produce undesirable side effects or have such degrees of toxicity that the use thereof is not practical. For example, while ordinary soap (salts of long chain aliphatic acids) is a very mild and well-tolerated prophylatic composition, the activity of soap is restricted to a relatively narrow group of microbes. On the other hand, methanol is effective against a relatively wide range of microbes, but produces considerable discomfort to the animal user when applied to open tissue, sensitive skin or internal membranes. It is also toxic. Hexachlorophene is active against a relatively wide range of microbes and is mild, but it has a possible undesired side effect, i.e., it has been indicated as a carcinogen.

In addition to the foregoing difficulties, special applications of microbicides impose even more stringent requirements. For example, where microbicides may be ingested by animals, e.g., humans, in substantial quantities, they must be non-toxic in ingested amounts. In this latter regard, the $LD_{50}$ of a microbicide may be higher when only small amounts would normally be ingested, for example, when used in cleaning eating utensils, in comparison with applications where larger amounts are nomally ingested, for example, when used to sanitize automatic milking equipment.

The most demanding applications in the foregoing regard, are when the microbicide is an ingredient in a composition that may be directly ingested, e.g., lipstick compositions, toothpaste, mouthwash and even in food compositions. This kind of application requires that the microbicide be "food-grade" and it is to this most stringent application that the present invention has particular relevance.

OBJECTS OF THE INVENTION

It is therefore an object of the invention to provide microbicidal and microbiostatic compositions and methods for producing microbicidal and microbiostatic effects with food-grade microbicides which are active against a wide range of microbes, including bacteria, fungi and protozoa. It is a further object to provide such compositions and methods which are effective at low concentrations of the primary active microbicide. Other objects of the invention will be apparent from the following disclosure and claims.

BRIEF DESCRIPTION OF THE INVENTION

Briefly stated, the present invention is based on the discovery that mono-esters of a twelve carbon atom aliphatic fatty acids and polyols unexpectedly provide very effective food-grade microbicides. Ideally, both the acids and polyols are chosen from recognized food-grade materials and, therefore, the resulting esters will also be food-grade.

The ester must be a mono-ester, i.e., not more than one of the available hydroxyl groups on the polyol may be esterified with the fatty acid.

The fatty acid may be branched or unbranched, saturated or unsaturated. If unsaturated, the kind of unsaturation and position of unsaturation can affect the resulting properties.

In the preferred embodiment, the fatty acid is the saturated straight-chain twelve-carbon atom acid, lauric acid, and the polyol is glycerol. This combination exhibits activity at a level surprisingly higher than the general activity of the present esters.

DETAILED DESCRIPTION OF THE INVENTION

The art has reported that some fatty acids and some derivatives thereof function as microbicides, particularly as bactericides. The lower chain fatty acids (i.e. below 12 carbon atoms) have been the fatty acids more usually described. However the art has taken very different views as to whether it is the parent acids, per se, or only the derivatives thereof, which are active. For exapmle, U.S. Pat. No. 2,321,595 describes bactericidal and bacteriostatic activities for primary amino-carboxylic acid esters of aliphatic polyhydroxy substances, partially esterified with fatty acids of eight to fourteen carbon atoms. (Also see U.S. Pat. No. 2,321,594 for a related disclosure.) On the other hand, an earlier disclosure, U.S. Pat. No. 1,917,681, indicates that aliphatic acids of 11 to 21 carbon atoms or derivatives thereof are bactericidal or bacteriostatic. But increased activity is described with acids having carboxyl group in the middle of the aliphatic chain. The disclosure then goes on to propose polyhydric alcohol esters of acids of the formula, $RCH(COOH)R^1$ as effective bactericides.

Uncertainty of the foregoing nature has continued in the art even to the present. For example, U.S. Pat. No. 3,331,742 discloses that only a bacteriostatic carrier for pharmaceuticals is provided when partial esters of saturate fatty acids below $C_{12}$ fatty acids (especially $C_6$ to $C_{10}$ fatty acids) are sterilized. In Glassman, H.N., "Surface Active Agents and their Application in Bacteriology," Bact. Rev. 12:105(1949), it is stated that although free long-chain fatty acids may be inhibitory to many microorganimsm, the same compounds esterified or formed into complexes with native serum albumin may have these toxic effects minimized or eradicated, and the resultant toxic compounds may actually enhance the growth of certain bacteria.

Experimental data in the art also showed that when the fatty acids are converted into surface-active compounds, that only the ionic derivatives are active. This was explained by the theory that the outer portions of bacteria are charged and that only charged surface-active agents would, therefore, be effective. Thus, non-ionic derivatives were considered to be inactive and this required the use of undesired ionic moieties, some of which produced derivatives of high or low pH and some toxicity, e.g. the quaternary derivatives.

As a result of all of these uncertainties, fatty acids and their derivatives have never been widely used in microbicide applications.

In part, the present invention is based on several discoveries which explain the above noted uncertainties and inconsistencies and which have allowed selections in this art to arrive at a highly effective, but yet food-grade microbicides. The first discovery is that the parent fatty acids can have microbicide properties, but that these properties vary in a rather non-uniform manner with chain length. Secondly, unsaturation in the acid chain can cause differences in activity and even different results may be experienced with the number, positions and type of unsaturations. Lastly, results obtained for parent acids are not necessarily translatable to the derivatives thereof and even within homologous derivatives significantly different results are obtained.

The above lead to the discovery that highly effective and yet food-grade microbicides are provided by mono-esters of a polyol and a twelve-carbon atom aliphatic carboxylic fatty acid. These esters must be mono-esters. Polyesters, e.g., diesters, triesters, ets., may not be used.

The primary microbicides may be formulated with a carrier to provide a microbicidal composition which is added to food or a food-grade material. Alternately, the primary microbicide may be added directly to a food or food-grade material. In all of these cases, the result is defined and used hereinafter as a "food-grade" composition which will, of course, comprise a food or a food-grade material or both. A food is defined as any digestable nutrient for animals, including humans while a food-grade material simply means that it is non-toxic and may be ingested in substantial quantities.

The polyol suitable for the invention may be any non-toxic polyhydroxylated aliphatic compound, i.e., having two or more hydric moieties. For example, there may be used a glycol such as propylene glycol, or a polyalkylene glycol such as polyethylene glycol, or polypropylene glycol or a poly-glycerol. Alternately, the polyol may be a non-toxic polyhydroxylated cyclic polyol such as sucrose, lactose cellulosic ethers or inositol, etc. However, the larger and more bulky polyols tend to increase water-solubility and affect other desirable handling properties. Further, the esters prepared from bulky polyols are generally less active than the more simple and less bulky polyol esters. For these reasons, overall superior results are obtained with more simple polyols, expecially those of less than 8 carbon atoms. Preferred polyols are trihydric aliphatic alcohols of less than 6 carbon atoms, such as glycerol. Thus, the best mode of the invention is the mono-ester, where R is the lauric acid residue.

The concentration of the present ester primary microbicide in the food-grade composition can vary widely and depends, essentially, on only the desired formulations. This is true since these compounds have no $LD_{50}$ (in the usual sense of the word). The parent acids are FDA-GRAS materials. When a similar food-grade polyol is used, the compounds could even be a food. However, the concentration of the present primary microbicides for a microbicidal or microbiostatic effective amount, generally, will be less than 30% by weight of the total food-grade composition, especially less than 20% or 15%, by weight, and usually from 0.001% to 2% by weight, the weight percentages being calculated on the basis of the weight of the free fatty acid. (If desired, non-toxic food-grade microbicides, e.g., bactericides and fungicides, in addition to the present primary microbicides, may be included in the composition, and these will be contained in the composition in amounts equal to or less than their respective customary maximum effective amounts, which are well known to the art.)

The above noted maximum concentrations of the present microbicides are observed unless concentrated formulations for subsequent dilution are intended. On the other hand, as will be illustrated by the examples, the minimum concentration of the primary microbicide for a microbicidal or microbiostatic effective amount, e.g., a bactericidal or bacteriostatic effective amount, may be quite low. the present esters are effective microbicides in exceedingly dilute concentrations, even as low as less than a hundredth of a micromole per milliliter of composition. (The bacteriostatic activity was still maintained at 0.01 $\mu$M/ml concentration in Example 3.)

Of course, coloring agents, extenders, diluents, fillers, flavors, and the like, may be included, as is known in the art. The food-grade composition may be in the form of suspensions, pastes, solutions, jellies, creams and ointments, with or without conventional thickening agents such as carboxy methylcellulose, gelatins and the like. Likewise, sprays and mists may be prepared according to conventional formularies. Further, conventional soaps, detergents, and the like may be formulated with the present bactericides. Of course the microbicides may be present in any conventional food, food-stuff or food additive. Accordingly, the compositions of the invention may be used on inanimate objects and materials or on animals, including humans, for effecting microbicidal or microbiostatic action. For example, the compostions may effect bactericidal or fungicidal action on apparatus and utensils used in clinical procedures, in pharmaceutical manufacture, food processing equipment, toothpaste, mouthwash, lipsticks, pharmaceuticals and food such as dairy products (milk, ice cream and cheese spreads), meat products (prepared meats and spreads) fruit and vegetable products (canned and frozen mushrooms, tomatoes, pears, etc.) and cereal products (breads, cakes and pies). Of course, if desired, the compositions may be used for non-food-grade applications such as for effecting bactericidal fungicidal or protozocidal action on the bodies of animals.

The rate of application of the ester for microbicidal or microbiostatic activity is not critical and is chosen for practical application depending on the final use form. The concentration of the ester should be at least 0.01 micromoles per milliliter (calculated as the free acid) of the composition, food or mantle containing the ester. This will at least produce a microbiostatic condition. Since the compounds are non-toxic there is no upper limiy to their use in unsual applications.

Solutions of the compositions are often important forms. Accordingly, the primary bactericide is preferably contained in a water dissolvable or dispersible carrier. More preferably, the carrier is an aqueous medium, e.g. essentially water, although other non-toxic solvents may be used. In foods, of course, the importance of the composition being water soluble or dispersible is considerably less. Very suitably, the composition may be simply in or on a solid food or food-grade carrier or in an oil or fat carrier.

The invention will be illustrated by the following examples, but the invention is not limited thereto and is fully applicable to the foregoing disclosure.

EXAMPLE I

In order to establish comparative bactericidal and fungicidal results with homologous fatty acids, a series of experiments was performed with thirty straight-chain fatty acids and derivatives thereof. Eight different gram-negative and twelve different gram-positive organisms, representing a very broad spectrum of organisms, were used in these experiments including the fungus candida (a yeast). Additionally, fatty acids were chosen to show the effects of saturation versus unsaturation, as well as the superior effects obtained when the unsaturation is a $C_{18:2}$* material. Standard solutions of the fatty acids and their derivatives were prepared by first dissolving the weighed compounds in 1 to 2 ml of 95% ethanol and immediately pouring this solution into 200 ml of Tripticase Soy Broth. Those lipid compounds which are insoluble in water and broth precipitated into very small crystals or droplets. The tubes containing the suspension were warmed to approximately 70° C and were then placed in an ultrasonic tank for further solubilization of the lipid derivatives.

*Chain unsaturation is designated by the symbol $\Delta°$, where ° indicates the position of unsaturation, with the carboxyl carbon as carbon number 1. The number of carbons in the fatty acid chain and the number of unsaturated bonds are indicated by the respective number joined by a colon. Thus, 2 - octadecenoic acid is $\Delta^2$ 18:1.

Standard solutions (or suspensions) at 1,000 μg/ml were twofold serially diluted with additional broth to a concentration of 125 μg/ml. A 4-ml amount of each dilution was then quickly, and with constant agitation, dispensed into appropriately labeled screw-capped glass tubes (16 by 125 mm). The tubes were sterilized with steam at 15 psi for 15 minutes. After sterilization, all tubes were cooled and incubated overnight at 35° C to insure sterility.

If a compound was found to have inhibitory activity at concentrations lower than 125 μg/ml, the testing was continued to a final concentration of 1.5 μg/ml for each active compound. All compounds were compared on a molar (micromoles/milliliter) rather than on a mass basis. In the following lists of organisms used, those followed by a parenthetical number are registered with the American Type Culture Collection; the remainder were isolates from Providence Hospital or Northland Laboratory.

Gram-positive organisms:
*Staphylococcus aureus*, *S. epidermidis*, beta-hemolytic streptococci (Group A and non-group A), group D streptococcus, *Bacillus subtilis* (6051), *Sarcina lutea* (9431), Micrococcus sp., *Candida albicans*, *Nocardia asteroides* (3308), Corynebacterium sp. (10700), and phenmococcus (63001).

Gram-negative organisms:
*Proteus vulgaris*, *P. mirabilis* (14273), *P. rettgeri* (9250), *Escherichia coli*, *Serratia marcescens* (13880), *Enterobacter-Klebsiella*, *Pseudomonas aeruginosa* (10145), and *Salmonela typhimurium*.

Strain differences within a genus were not significant by the present mode of testing.

One drop (0.04 ± 0.10 ml) of an 18-hr broth culture containing $10^9$ to $10^{12}$ organisms/ml was added to each dilution of the test compound, as well as to a tube of plain broth which served as the positive control. After inoculation, the contents of each tube were well mixed, and the tubes were incubated at 35° C in a 5% carbon dioxide + 95% oxygen atmosphere.

After 18 hours of incubation, the minimal inhibitory concentration (MIC) of each compound was determined for each microorganism. The MIC is defined as the lowest concentration of compound at which no microscopic evidence of growth was obsserved when turbidity of the inoculated broth dilutions was compared with control tubes. In those instances in which the test compound itself caused turbidity so that the MIC could not accurately be determined, a sample (0.015 ml) of the well-agitated broth was inoculated into a Trypticase Soy Agar plate containing 5% defibrinated sheep blood, incubated at 35° C, and examined after 18 hours for bacteriostatic and bactericidal end points. Only a one-tube difference between the bactericidal and bacteriostatic concentrations was normally observed.

To test the effects of the sterilization procedure on the stability of the unsaturated fatty acids, a control series was undertaken with 10mg each of oleic and linoleic acid. Each sample was dissolved in absolute methanol, and the volume was reduced in vacuo to 0.25 ml of the compound, and appropriate dilutions were made from this stock solution. The activity of these solutions was compared with that of sterilized controls.

As a comparison of effectiveness, a well-known surface-active agent, sodium sulfate was used as a control. Such surface active agents are not active at concentrations > 1000 μg/ml.

Because insolubility of the compound is always a problem in testing lipid material, a control series was undertaken to investigate the effect of particulate suspensions on the bactericidal property. Particularly, the relationship of insolubility of a fatty acid to its biological activity was determined by a series of experiments in which lauric acid was used as the model compound as follows. A suspension of lauric acid, as well as a filtrate of the same suspension, was tested for antimicrobial activity. Bio Gel and Florisil were mixed with lauric acid-containing broth to remove particulate matter before it was filtered. Albumin (Miles Pentex, Fatty-Acid Free) to a final concentration of 1.1% was added to a suspension of lauric acid to study the effect of added protein on biological activity.

The data for nine gram-positive organisms and the yeast/fungus Candida are presented in Tables 1 and 3; Tables 2 and 4 give the range of activities as well as the maximal concentration tested; Table 5 presents a comparison of the $C_{10}$ and $C_{12}$ free acids and their glyceryl derivatives; and Table 6 gives the corresponding ranges of activity.

Both methods of compound addition (pre- or post-sterilization) gave identical results except with linolelaidic acid. Repeat tests showed that the results for this fatty acid were variable and were dependant on the time, temperature, and pressure of autoclaving. For this compound, the results from the nonsterilized procedure were used.

While not shown in the tables sodium lauryl sulfate was noninhibitory for gram-negative organisms, and was inhibitory at 3.47 $\mu$ moles/ml, but not less than 0.347 $\mu$moles/ml, for gram-positive organisms. The compound is active in solution or in suspension.

Broth with laurate crystals removed was less inhibitory than non-filtered broth. For groaup A streptococci, the results were 0.125 $\mu$ mole/ml as compared to 1.0 $\mu$ mole/ml (filtered). When Bio Gel and Florisil were used, the inhibition was reduced to greater than 0.99 $\mu$ mole/ml. Albumin (0.1%) had no effect on the determination of the MIC under the conditions of the experiments.

Microorganisms were arranged by degree of susceptibility.

As can be seen from Table 1, and as summarized by Table 2, there is a substantial difference in activity of the saturated acids. Thus, caproic acid, $CH_3(CH_2)_4COOH$, was not inhibitory at all, as was the case with stearic acid, $CH_3(CH_2)_{16}COOH$. Between this $C_6$ to $C_{18}$ saturated acid range, varying degrees of activity can be seen, but lauric acid is clearly the more active saturated acid.

The effects of unsaturation point up how unpredictable is the microbiological activity of these long chain acids. Not only does unsaturation have an effect (myristoleic/myristic and palmitoleic/palmitic) but the cis/trans isomers have an effect (oleic/elaidic), as well as the specific amount of unsaturation (linoleic/linolenic/ linolelaidic acids) and the chain length with the unsaturation (arachiodonic acid).

The unpredictability of the activity of long chain acids is further illustrated by Table 3, and as summarized by Table 4, where the corresponding alcohol, aldehyde, lower ester, higher ester, amine, aide, thiol and unsaturate of lauric acid are compared with lauric aciditself. As can be seen, only the amine and the amide showed activity comparable to the parent acid, but the compounds are not food-grade compounds.

Unsaturation appears to make the longer chains fatty acids ($>C_{14}$) more active while there is little effect for shorter chain fatty acids.

Unsaturation, generally increases activity against yeast (fungus) as contrasted to effects on bacteria. Shorter chain lengths unsaturated esters are active against yeast.

Table 5 shows, as summarized in Table 6, a comparison between lauric acid and capric acid and their glyceride esters. Extremely striking results are obtained. For both the capric and lauric acids the mono-glycerides (1, or 2 mono-) are active while the di (1, 2 or 1,3) and tri-glycerides are inactive. This is most surprising and unexpected. Further, the mono-laurin was significantly more active than the mono-capric, with the sole exception of the streptococcus Group D organisms. In all other cases, the mono-laurin ranged from essentially as active to 5.5 times more active, a most surprising and unexpected result. Also note that essentialy the 1-mono-laurin is as active as the 2-mono-laurin.

Example II

This example compares the effects of polyhydric alcohol esters of the fatty acids.

Standard solutions (1000 g/ml) of three fatty acids and polyglycerol esters thereof were prepared as described in Example I. Also sucrose esters were prepared by transferring the weighed compounds (0.2 gm. dissolved in 1 ml absolute methanol) into 200 ml of sterile Trypticase Soy Broth (TSB). These standard solutions (1000 $\mu$g/ml) were twofold serially diluted with additional sterile broth to a concentration of 125 $\mu$g/ml. A 3.8 aliquot of each dilution was asceptically delivered into sterile screw-capped culture tubes. All tubes were incubated overnight at 36° C to insure sterility.

The microorganisms used in this example were the same as those used in Example I.

The inoculum, 0.5 ml of an 13–24 hour TSB culture (approximately $10^9$ organisms/ml) was asceptically delivered into al dilutions of the compounds, mixed well, and incubated at 36° C. A tube of inoculated broth without compound served as a positive control and an uninoculated set of dilutions incubated along with the test dilutions, served as a negative control.

After 18-hours of incubation, the Minimal Inhibitory Concentration (MIC) of each compound was determined for the organisms tested. In those cases in which the test compound itself caused turbidity, an aliquot (0.015 ml) of the mixed broth was inoculated onto an agar plate and incubated at 36° C for examination, as described in Example I. The control procedure of Example I was also repeated. The lauric, capric, and oleic acids were used as internal controls and for comparison to Example I.

The minimal inhibitory concentrations ($\mu$mol/ml) for the compounds studies are given in Tables 7 and 8.

Table 7 shows the MIC's for the polyglycerides and compares the same with the free acid form. The tri-and hexaglycerol monocaprates have greater inhibition in some cases than the free acid form but the spectrum is not as wide as the free acid form. They do not inhibit the Staphylococci or Group D Strep.

The tri-, hexa-, and decaglycerol monolaurates have less inhibition than the free acid form. These polyglycerol monolaurates do not inhibit the staphylococci or Group D strep.

Triglycerol oleate had no activity at the concentration tested while the free acid form had very limited activity.

Table 8 compares various sucrose esters with lauric acid. Sucrose esters, except for laurate, are more active in some cases than the free acid form, but their antmicrobial spectrum of activity is more limited. None of the sucrose esters tested inhibit Staphylococcus aureus or Group D Strep. Sucrose palmitate is the only ester which inhibits S. epidermis and Sarcina. Table 9 shows the analytical results of the composition of the sucrose esters, with the exception of sucrose caprate.

While not shown in the tables, two other lauric acid derivatives were tested against six organisms. Thus, α-hydroxylaurate was active against Group A Strep (0.23 μmol/ml and *Nocardia asteroides* (4.63 μmol/ml). Methyl, α-hydroxylaurate was inhibitory to *S. aureus*, Group A Strep, and *Saccharomyces cerevisiae* (0.54 μmol/ml) and *Nocardia asteroides* (4.34 μmol/ml). Neither compound was inhibitory for Group D Strep and *E. coli*.

Example III

From Examples I and II it can be seen that fatty acid chain length and unsaturation can have effects on the bactericidal activity of the fatty acids. This example shows the activity in more detail.

Examples I and II show that the Group A β-hemolytic streptococci organism gives results typical of the results of all of the organisms for a particular fatty acid or derivative. Therefore, to simplify the testing procedure, this typical organism is used in this Example.

Similarly to Examples I and II, solutions of potassium soaps of certain fatty acis were inoculated with 0.05 ml of an 18-hour broth culture of a virulent Group A β-hemolytic streptococci. Acid concentrations after the second dilution, (ph 7.6) had no appreciable effect on the pH of the media. The minimal inhibitory concentration (MIC) in μM/ml for each acid was determined after an overnight incubation of the acid and microorganism at 35° C in a 5% $CO_2$ + 95% $O_2$ atmosphere in a manner similar to Examples I and II.

Figure 1:
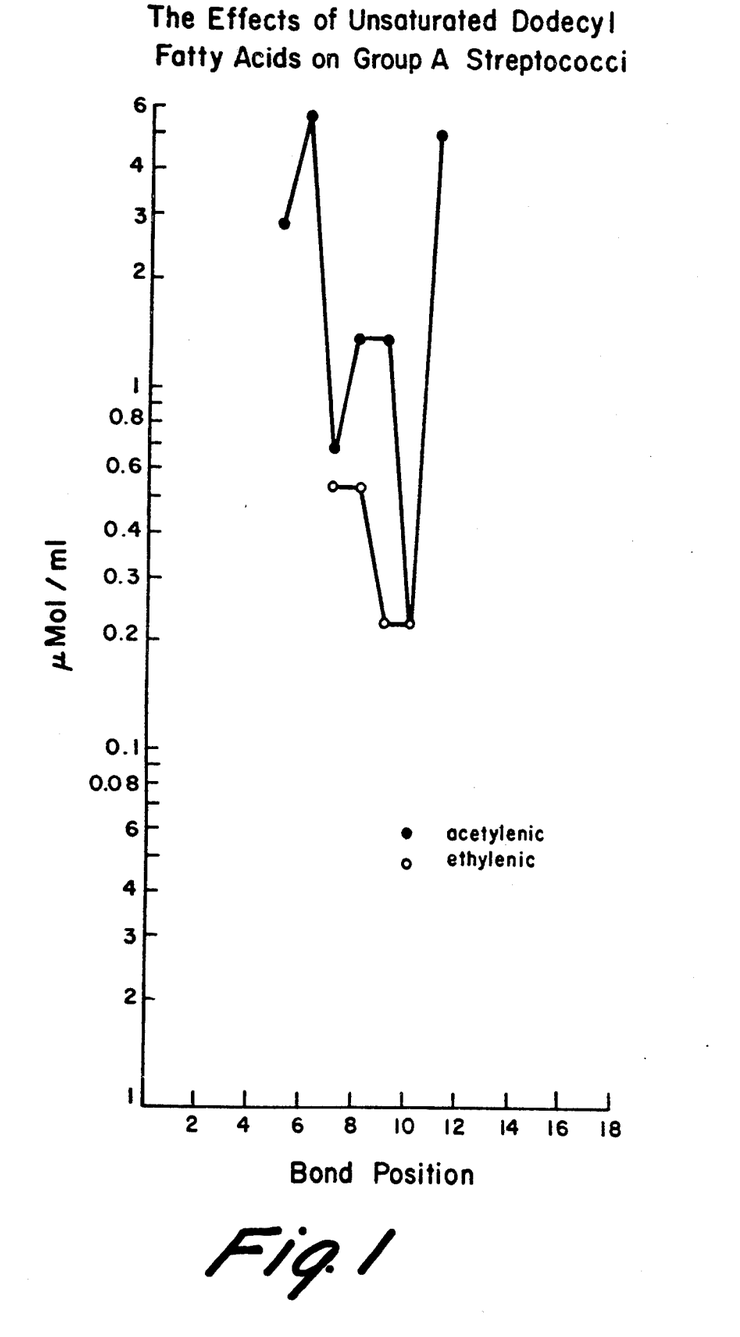
FIG. 1 shows a comparison between ethylenic and acetylenic unsaturation of twelve-carbon atom fatty acids.

The results for the $C_{12}$ acids are presented in FIG. 1. Generally, the ethylenically unsaturated acids were more active toward the Group A streptococci than the corresponding acetylenically unsaturated acids. The greatest difference between these two types of unsaturation is found with the $\Delta^9$ isomer. For both types of unsaturation the $\Delta^{10}$ isomer was the most active.

Figure 2:
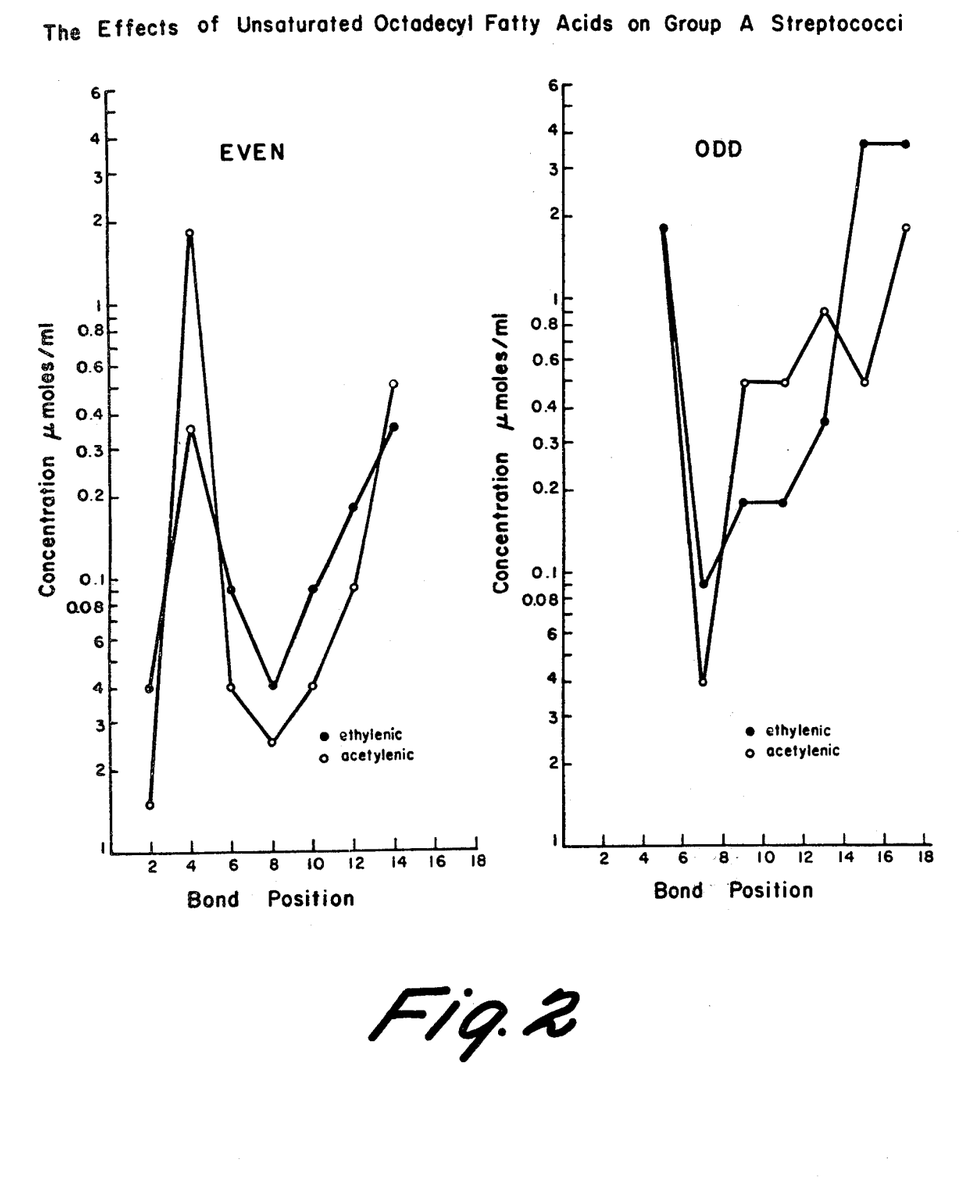
FIG. 2 shows the unpredictable effects of unsaturation by way of eighteen carbon atom fatty acids.

By comparison, as shown in FIG. 2, the $C_{18}$ acids were more active toward Group A streptococci than the $C_{12}$ acids. This data is divided into two homologous series of isomers, i.e., odd vs. even carbon chain length. For each series the ethylenically unsaturated acids are generally less active than acetylenically unsaturated acids. However, since the data for $\Delta^6$, $\Delta^8$, $\Delta^{10}$, $\Delta^{12}$, $\Delta^{14}$, $\Delta^{17}$ isomers represent only one tube difference in the testing procedure, it is not necessarily significant. Differences between ethylenically and acetylenically unsaturated acids at positions $\Delta^4$ and $\Delta^{15}$ are, however, significant. Greater inhibitory activity for both types of unsaturation is noted when the unsaturation is in the $\Delta^2$, $\Delta^7$ or $\Delta^8$ positions.

The effect of a second double bond and its positional isomers is seen from 18:2 acids. These acids are more active than the 18:1 series. For comparative purposes, individual monoenoic isomers (two) which have unsaturation in similar positions to the dienoic molecule, are compared to the dienoic acid, i.e., the $\Delta^{9,12}$ 18:2 is compared to the $\Delta^9$ 18:1 and the $\Delta^{12}$ 18:1. The differences are listed in Table 10. In such a comparison, the activity of the 18:2 is always greater than the component 18:1 isomers. Usually the more unsaturated fatty acids are 8-15 fold more toxic.

Example IV

Figure 3:
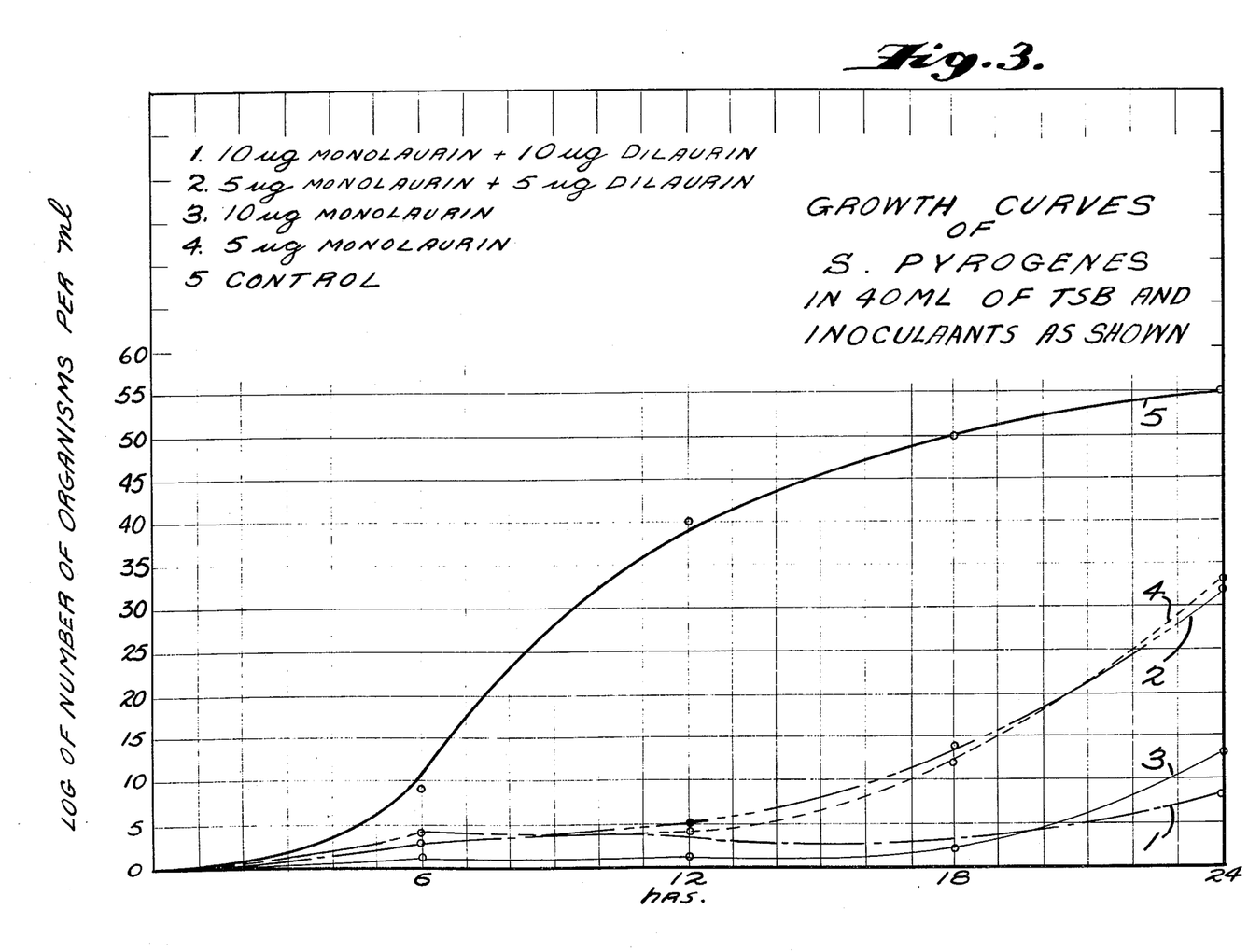
FIG. 3 shows the growth curve of S. pyrogenes in comparing glycerol mono-esters and diesters of lauric acid.

To a series of containers is added 40 ml of Trypticase Soy Broth and 0.5 ml of streptococcus pyrogenes ($10^8$ organisms/ml). To respective containers are added the following: (1) μg of glycerol 1-mono-laurin and 10 μg of glycerol dilaurin; (2) 5 μg of glycerol 1-mono-laurin and 5 μg of glycerol dilaurin; (3) 10 μg of glycerol 1-mono-laurin; and (4) 5 μg of glycerol 1-mono-laurin; and (5) a control without any additives. The rate of growth of the *S. pyrogenes* was followed for 24 hours at 6 hour intervals by reading the optical density of the cultures at 550 mm in a spectrophotometer. The results are shown in FIG. 3. As can be seen, the test with 1-mono-laurin alone gave essentially the same results as when tested with equal amounts of dilaurin. Thus, the dilaurin is essentially inactive while the mono-laurin is responsible for all antimicrobial activity.

From the foregoing Examples, it can be seen that predictability of biological activity for long-chain fatty acids and derivatives thereof is exceedingly low. Chain length, saturation or unsaturation (as well as the type of unsaturation and position thereof) and the type of derivative (as well as variations in the degree of substitution of its derivative, e.g. mono- versus di- or tri-) can cause significant variations in activity toward one organism and other variations towards groups of different organisms.

Such unpredictable results have probably been the reason for the contradictory conclusions and statements in the art as to the activity or lack of activity of long-chain fatty acids and derivatives thereof. These contradictory results and conclusions have discouraged attempts at using these materials as antimicrobial agents.

Thus, the experimental results, upon which the present invention is based, points out the superior materials within the class of long-chain fatty acids and the derivatives thereof. The mono-laurin derivatives provide unique combinations of properties, i.e., food-grade, active toward a wide spectrum of both gram-positive and gram-negative organisms, yeast and protozoan active at low concentrations. Thus, the mono-laurins constitute a distinct class of compounds within the present invention with unique and unexpected superior results and constitute the preferred esters of the invention.

The invention has been described above and is applicable to the scope of the annexed claims. However, it is also apparent that modifications thereof may be practiced and the claims are intended to embrace those apparent modifications.

TABLE 1

| | MIC OF 15 FATTY ACIDS (μMol/ml) | | | | | | | | | |
|---|---|---|---|---|---|---|---|---|---|---|
| Organism | Pneumo-cocci | Strepto-coccus Group A | Strepto-coccus beta-he-molytic Non-A | Coryne-bacteria | Nocardia asteroides | Micro-cocci | Candida | S. aureus | S. epider-midis | Strepto-coccus Group D |
| Compound | | | | | | | | | | |
| Caproic | NI* | NI | NI | NI | NI | NI | NI | NI | NI | NI |
| Caprilic | NI | NI | NI | NI | NI | NI | NI | NI | NI | NI |
| Capric | 1.45 | 1.45 | 2.9 | 1.45 | 1.45 | 2.9 | 2.9 | 2.9 | 2.9 | 5.8 |
| Lauric | .062 | 0.124 | 0.249 | 0.124 | 0.124 | 0.624 | 2.49 | 2.49 | 2.49 | 2.49 |

TABLE 1-continued

MIC OF 15 FATTY ACIDS (μMol/ml)

| Organism | Pneumo-cocci | Strepto-coccus Group A | Streptococcus beta-hemolytic Non-A | Coryne-bacteria | Nocardia asteroides | Micro-cocci | Candida | S. aureus | S. epidermidis | Streptococcus Group D |
|---|---|---|---|---|---|---|---|---|---|---|
| Myristic | 0.218 | 0.547 | 2.18 | 0.437 | 0.547 | 0.547 | 4.37 | 4.37 | 2.18 | 4.37 |
| Myristoleic | 0.110 | 0.110 | 0.110 | 0.055 | 0.110 | 0.220 | 0.552 | 0.441 | 0.441 | 0.441 |
| Palmitic | 0.48 | 3.9 | 3.9 | 1:9 | NI | 1.9 | NI | NI | 3.9 | NI |
| Palmitoleic | 0.024 | 0.098 | 0.049 | 0.049 | 0.049 | 0.049 | 0.491 | 0.983 | 0.491 | 0.491 |
| Stearic | NI | NI | NI | NI | NI | NI | NI | NI | NI | NI |
| Oleic | NI | 1.77 | NI | NI | NI | NI | NI | NI | NI | NI |
| Elaidic | NI | NI | NI | NI | NI | NI | NI | NI | NI | NI |
| Linoleic | 0.044 | 0.089 | 0.089 | 0.044 | 0.089 | 0.089 | 0.455 | NI | NI | NI |
| Linolenic | 0.179 | 0.35 | 0.35 | 0.179 | 0.488 | 0.488 | NI | 1.79 | NI | NI |
| Linolelaidic | NI | NI | NI | NI | NI | NI | NI | NI | NI | NI |
| Arachidonic | NI | NI | NI | NI | NI | NI | NI | NI | NI | NI |

*NI - Not inhibitory at the concentrations tested (1.0 ·,g/ml or 3 to 6.0 μmol/ml).

TABLE 2

MIC RANGES (μMol/ml)

| Compound | Range | Max. tested |
|---|---|---|
| Caproic | NI | 10 |
| Caprilic | NI | 7.8 |
| Capric | 1.45–5.8 | 5.8 |
| Lauric | 0.062–2.49 | 4.9 |
| Myristic | 0.218–4.37 | 4.37 |
| Myristoleic | 0.055–0.552 | 4.4 |
| Palmitic | 0.48–NI | 3.9 |
| Palmitoleic | 0.024–0.983 | 3.93 |
| Stearic | NI | 3.5 |
| Oleic | 1.77–NI | 3.54 |
| Elaidic | NI | 3.54 |
| Linoleic | 0.044–NI | 3.56 |
| Linolenic | 0.179–NI | 3.59 |
| Linolelaidic | NI | 3.59 |
| Arachidonic | NI | 3.2 |

TABLE 4

MIC Ranges of Dodecyl Compounds (μMol/ml)

| Compound | Range | Max. tested |
|---|---|---|
| Lauric acid | 0.062–2.49 | 4.9 |
| Lauryl alcohol | 0.067–5.4 | 5.4 |
| Laurylaldehyde | 0.136–NI | 5.4 |
| Methyl laurate | 2.3–NI | 4.6 |
| Lauryl acetate | NI | 4.38 |
| Cholesteryl laurate | NI | 1.76 |
| Dodecylamine HCl | 0.028–0.112 | 4.5 |
| Lauryl N,N-di-methylamide | 0.054–0.109 | 4.39 |
| 1-Dodecane-thiol | NI | 4.94 |
| Dodecanedioic acid | NI | 4.3 |

TABLE 3

MIC OF DODECYL COMPOUNDS (μMol/ml)

| Organism | Pneumo-cocci | Streptococcus Group A | Streptococcus Beta-he Molytic Non-A | Coryne-bacteria | Nocardia asteroides | Micro-cocci | Candida | S. aureous | S. epider-midis | Streptococcus Group D |
|---|---|---|---|---|---|---|---|---|---|---|
| Compound | | | | | | | | | | |
| Lauric acid | 0.062 | 0.124 | 0.249 | 0.124 | 0.124 | 0.624 | 2.49 | 2.49 | 2.49 | 2.49 |
| Lauryl alcohol | 0.067 | 0.067 | 0.271 | 0.135 | 0.135 | 0.135 | 0.135 | 0.271 | 0.135 | 5.4 |
| Laurylaldehyde | 0.136 | 0.136 | 0.136 | 0.136 | 0.136 | 0.54 | 0.136 | 0.272 | 0.272 | NI |
| Methyl laurate | — | 4.6 | NI | 4.6 | 4.6 | 2.3 | 4.6 | NI | NI | 4.6 |
| Lauryl acetate | NI | NI | NI | NI | NI | NI | NI | NI | NI | NI |
| Cholesterol laurate | NI | NI | NI | NI | NI | NI | NI | NI | NI | NI |
| Dodecylamine HCl | 0.056 | 0.056 | 0.112 | 0.028 | 0.112 | 0.112 | 0.112 | 0.112 | 0.112 | 0.112 |
| Lauryl N,N-di-methylamide | 0.054 | 0.054 | 0.109 | 0.054 | 0.054 | 0.109 | 0.109 | 0.109 | 0.109 | 0.109 |
| 1-Dodecane-thiol | NI | NI | NI | NI | NI | NI | NI | NI | NI | NI |
| Dodecanedioic acid | NI* | NI | NI | NI | NI | NI | NI | NI | NI | NI |

*NI- Not inhibitory at the concentrations tested.

TABLE 5

MIC Comparison (μMol/ml) Free Acid Form vs. Glyceride Form

| Organism | Pneumo-cocci | Strep. Grp. A. | Strep. β-hemo. Non-A | Coryne-bacteria | Nocardia asteroides | Micro-cocci | Candida | Staph aureus | Staph epid. | Strep. Grp. D |
|---|---|---|---|---|---|---|---|---|---|---|
| Compound | | | | | | | | | | |
| Capric acid | 1.45 | 1.45 | 2.90 | 1.45 | 1.45 | 2.90 | 2.90 | 2.90 | 2.90 | 5.80 |
| 1-mono-caprin | 0.10 | 0.20 | 0.20 | 0.20 | 0.50 | 0.10 | 1.00 | 1.00 | 1.00 | 2.00 |
| 1,3-dica-prin | | | — | NO INHIBITION | (>3.30)* | — | | | | |
| Lauric acid | 0.06 | 0.12 | 0.25 | 0.12 | 0.12 | 0.62 | 2.49 | 2.49 | 2.49 | 2.49 |
| 1-mono-laurin | 0.09 | 0.05 | 0.09 | 0.05 | 0.09 | 0.09 | 0.09 | 0.09 | 0.09 | >5.63* |

TABLE 5-continued

MIC Comparison (μMol/ml)
Free Acid Form vs. Glyceride Form

| Organism | Pneumo-cocci | Strep. Grp. A. | Strep. β-hemo. Non-A | Coryne-bacteria | Nocardia asteroides | Micro-cocci | Candida | Staph aureus | Staph epid. | Strep. Grp. D |
|---|---|---|---|---|---|---|---|---|---|---|
| 2-mono-laurin | —** | 0.09 | 0.19 | 0.19 | 0.19 | 0.09 | — | 0.19 | 0.09 | >3.63* |
| 1,2-di-laurin | | | — | NO INHIBITION (>2.18)* | | — | | | | |
| 1,3-di-laurin | | | — | NO INHIBITION (>2.18)* | | — | | | | |
| trilaurin | | | — | NO INHIBITION (>1.56)* | | — | | | | |

*No inhibition [Max.] tested listed.
**Not tested

TABLE 6

MIC Ranges of Free Acid Form with Glyceride Form (μ/Mol/ml)

| Compound | Range | Max. Tested |
|---|---|---|
| Capric Acid | 1.45–5.8 | 5.8 |
| 1-mono-caprin | 0.1–2.0 | 4.04 |
| 1,3-dicaprin | NI | 3.3 |
| Lauric acid | 0.062–2.49 | 4.9 |
| 1-mono-laurin | 0.045–NI* | 3.63 |
| 1,3-dilaurin | NI | 2.18 |
| Trilaurin | NI | 1.56 |

*Highly active on all organisms except streptococcus Group D which is non-inhibitory.

TABLE 7

MIC Comparison (μMol/ml)
Free Acid Form vs. Polyglyceride Form

| Organism | Strep. Grp. A | Strep. β-hemo. Non-A | Corne-bacteria | Micro-cocci | Sarcina | Staph aureus | Staph epider. | Strep. Grp. D |
|---|---|---|---|---|---|---|---|---|
| Compound | | | | | | | | |
| Capric acid | 1.45 | 2.90 | 1.45 | 2.90 | — | 2.90 | 2.90 | 5.80 |
| Triglycerol monocaprate | 0.15 | 0.63 | 0.32 | 1.26 | 2.50 | >2.50* | >2.50* | >2.50* |
| Hexaglycerol monocaprate | 0.19 | 0.79 | 0.39 | 0.79 | >1.58* | >1.58* | >1.58* | >1.58* |
| Lauric acid | 0.12 | 0.25 | 0.12 | 0.62 | 2.49 | 2.49 | 2.49 | 2.49 |
| Triglycerol monolaurate | 0.29 | 0.59 | 0.24 | 0.29 | 1.18 | >2.36* | >2.36* | >2.36* |
| Hexaglycerol monolaurate | 0.19 | 0.38 | 0.38 | 0.38 | >1.52* | >1.52* | >1.52* | >1.52* |
| Decaglycerol monolaurate | 0.26 | 0.53 | 0.53 | 0.53 | >1.06* | >1.06* | >1.06* | >1.06* |
| Oleic acid | 1.77 | — | — | — | NO INHIBITION | (>3.54)* | — | |
| Triglycerol oleate | | | | — | NO INHIBITION | (>1.98)* | — | |

*No inhibition [Max.] tested listed.

TABLE 8

MIC (μMol/ml)
Effectiveness of Sucrose Esters[1]

| Organism Compound | Pneumo-cocci | Strep. Grp. A | Coryne-bacteria | Nocardia asteroides | Micro-cocci | Sarcina | Staph. epider. |
|---|---|---|---|---|---|---|---|
| Lauric acid | 0.06 | 0.12 | 0.12 | 0.12 | 0.62 | 2.49 | 2.49 |
| Sucrose laurate | 0.12 | 0.03 (.12) | 0.47 (.23) | 0.47 (1.90) | 1.90 | >1.90* | >1.90* |
| Sucrose caprate | 0.06 | 0.06 | 0.25 | 0.25 | 1.00 | >2.00* | >2.00* |
| Sucrose myristate | 0.23 | 0.05 (.11) | 0.11 (.11) | 0.23 (.11) | 0.23 | >1.84* | >1.84* |
| Sucrose palmitate | 0.05 | 0.10 (.20) | 0.43 (.26) | 0.43 (>1.72*) | 0.26 | 0.43 | 0.86 |
| Sucrose elaidate | 0.20 | 0.20 | 1.64 | 0.20 | 0.82 | >1.64* | >1.64* |
| Sucrose oleate | 0.05 | >1.64* (.41) | >1.64*(>1.64*) | 0.41 (.21) | 0.21 | >1.64* | >1.64* |
| Sucrose linoleate | 0.05 | 0.41 (.82) | >1.66*(1.66) | 0.41 (1.66) | 0.82 | >1.66* | >1.66* |

*No inhibition, [Max.] tested listed
[1]Gram positive organisms not inhibited by sucrose esters are Staph. aureus, Bacillus subtillis and Grp. D Strep.

TABLE 9

Analytical Results of the Samples Sucrose Esters

| Sample | Sucrose Ester, % | Composition % Mono- | Di- | Tri- | Degree of Substitution | Composition of Fatty Acid | |
|---|---|---|---|---|---|---|---|
| Sucrose laurate | 90.3 | 58.3 | 34.0 | 7.7 | 1.39 | $C_{12}$ min. | 99% |
| Sucrose myristate | 89.3 | 61.5 | 33.6 | 4.9 | 1.34 | $C_{14}$ min. | 94% |
| Sucrose palmitate | 87.1 | 52.4 | 6.4 | 11.1 | 1.45 | $C_{16}$ min. | 93% |
| Sucrose | 67.9 | 60.2 | 32.8 | 7.0 | 1.35 | $C_{18:1}$ | 75.5% |
| | | | | | | $C_{18:2}$ | 11.5% |
| | | | | | | $C_{18}$ | 7.3% |
| | | | | | | $C_{16}$ | 5.2% |
| | | | | | | $C_{14}$ | 0.5% |
| Sucrose linoleate | 72.0 | 48.7 | 36.0 | 15.4 | 1.51 | $C_{18:2}$ | 52.6% |
| | | | | | | $C_{18:1}$ | 24.9% |
| | | | | | | $C_{18:3}$ | 7.9% |
| | | | | | | $C_{18}$ | 5.3% |
| | | | | | | $C_{16}$ | 8.2% |
| | | | | | | $C_{20}$ | 0.9% |

TABLE 10

Comparison of Ethylenic 18:2 vs. 18:1
MIC's Against Group A Strep. ($\mu$Mol/ml)

| DIENOIC | MONOENOIC | MIC | DIFFERENCE |
|---|---|---|---|
| $\Delta^{9,12}$ | | 0.01 | |
| | $\Delta^{12}$ | 0.18 | 0.17 |
| | $\Delta^{9}$ | 0.18 | 0.17 |
| $\Delta^{8,12}$ | | 0.02 | |
| | $\Delta^{12}$ | 0.18 | 0.16 |
| | $\Delta^{8}$ | 0.04 | 0.02 |
| $\Delta^{7,12}$ | | 0.02 | |
| | $\Delta^{12}$ | 0.18 | 0.16 |
| | $\Delta^{7}$ | 0.09 | 0.07 |
| $\Delta^{6,12}$ | | 0.01 | |
| | $\Delta^{12}$ | 0.18 | 0.17 |
| | $\Delta^{6}$ | 0.09 | 0.08 |
| $\Delta^{5,12}$ | | 0.02 | |
| | $\Delta^{12}$ | 0.18 | 0.16 |
| | $\Delta^{5}$ | 1.77 | 1.75 |
| $\Delta^{6,12}$ | | 0.01 | |
| | $\Delta^{6}$ | 0.09 | 0.08 |
| | $\Delta^{12}$ | 0.18 | 0.17 |
| $\Delta^{6,11}$ | | 0.02 | |
| | $\Delta^{6}$ | 0.09 | 0.07 |
| | $\Delta^{11}$ | 0.18 | 0.16 |
| $\Delta^{6,10}$ | | 0.01 | |
| | $\Delta^{6}$ | 0.09 | 0.08 |
| | $\Delta^{10}$ | 0.09 | 0.08 |

What is claimed is:

1. A microbicidal of microbiostatic food-grade composition comprising a food subject to microbial spoilage and therefore in need of preservation and containing in an effective amount of up to 30% by weight of a primary food-grade microbicide consisting essentially of a 1 or 2 -mono-laurin polyol ester as the sole active microbicide in the composition.

2. The composition of claim 1 wherein the said ester has the formula where R is the lauric acid residue.

3. A method for effecting a microbicidal action in a food subject to microbial spoilage and therefore in need of preservation; comprising adding thereto a microbicidally or microbiostatically effective amount of a food-grade microbicide consisting essentially of a 1 or 2-mono-laurin polyol ester as the sole active microbicide in the composition.

4. The method of claim 3 wherein the composition is ingested by an animal or human.

* * * * *